United States Patent [19]

Suzuki et al.

[11] Patent Number: 4,977,171

[45] Date of Patent: Dec. 11, 1990

[54] OXA- OR THIA-ZOLINE DERIVATIVE

[75] Inventors: Junji Suzuki; Tatsuya Ishida; Kazuya Toda; Tatsufumi Ikeda; Yokichi Tsukidate; Kikuchi Yasuo; Yoskiaki Itoh, all of Nagano, Japan

[73] Assignee: Yashima Chemical Industrial Co., Ltd., Tokyo, Japan

[21] Appl. No.: 360,866

[22] Filed: Jun. 2, 1989

[30] Foreign Application Priority Data

Jun. 9, 1988 [JP] Japan .................... 63-140547

[51] Int. Cl.$^5$ ...................... A01N 43/76; A01N 43/78
[52] U.S. Cl. ..................... 514/365; 514/374; 548/146; 548/237; 548/239
[58] Field of Search ............. 514/374, 365; 548/146, 548/239, 237, 238

[56] References Cited

U.S. PATENT DOCUMENTS

| | | | |
|---|---|---|---|
| 2,714,082 | 7/1955 | Davies | 514/374 |
| 3,268,544 | 8/1966 | Thompson | 548/146 |
| 3,440,247 | 4/1969 | Dorer et al. | 548/239 |
| 3,450,699 | 6/1969 | Seeliger et al. | 548/239 |
| 4,153,703 | 5/1979 | Harrison et al. | 514/365 |
| 4,443,611 | 4/1984 | Kaiser | 548/239 |
| 4,479,888 | 10/1984 | Koch et al. | 548/239 |

OTHER PUBLICATIONS

Gabriel et al., Ber., vol. 47, pp. 1866–1873 (1914).
Chem. Abstr., vol. 98, entry 16670c (1983), Abstract WO 82/02046.
Chem. Abstr., vol. 98, entry 160087k (1983) (Bazyl et al.).
Tetrahedron Letters, 22(45), 4471–4474 (1981).

Primary Examiner—Donald G. Daus
Attorney, Agent, or Firm—Wenderoth, Lind & Ponack

[57] ABSTRACT

A compound represented by the following formula

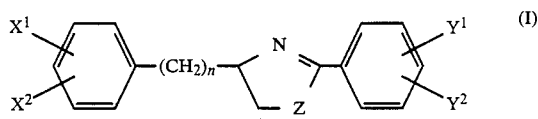

wherein
$X^1$ and $X^2$ are identical or different and each represents a hydrogen atom, a lower alkyl group, a lower alkoxy group, a halogen atom, a trifluoromethyl group or a trifluoromethoxy group;
$Y^1$ and $Y^2$ are identical or different and each represents a hydrogen atom, a lower alkyl group, a lower alkoxy group, a lower alkylthio group, a cyano group, a nitro group, a halogen atom or a trifluoromethyl group;
Z represents an oxygen or sulfur atom; and
n is 0 or 1;
excepting the case where n is 0 and $X^1$ and $X^2$ are both hydrogen atoms, the case where n is 1 and $X^1$ and $X^2$ are members selected from the class consisting of hydrogen and halogen (excepting iodine) atoms, and the case where $Y^1$ and $Y^2$ are membrs selected from the class consisting of hydrogen and halogen (excepting iodine) atoms and nitro groups. This compound is useful as an insecticidal and acaricidal (miticidal) agent.

9 Claims, No Drawings

OXA- OR THIA-ZOLINE DERIVATIVE

This invention relates to a novel oxa- or thia-zoline derivative, a process for its production, and use of it as an insecticidal and acaricidal (mitcidal) agent.

Some papers have been published on 2,4-diphenyl-2-oxa- or thia-zoline compounds. For example, see Chem. Ber., 47, 1866–1873 (1914); Tetrahedron Letters, 22 (45), 4471–4474 (1981); Chemical Abstracts, 98 (18), 160087k; and J. Org. Chem., 52, 2523–2530 (1987).

PCT International Application Publication No. WO 82/02046 (Schering AG) discloses 2,4-diphenyl-2-oxa or thia-zoline derivatives and 2-phenyl-4-benzyl-2-oxa- or thia-zoline derivatives.

These references, however, fail to disclose the biological activities, particularly insecticidal or acaricidal activities, of these compounds.

Insecticides and/or acaricides have been used to protect useful crops and plants from noxious insects and mites in agriculture, horticulture and forestry. Insects and mites parasitic on plants have been aquiring resistance to existing insecticides and/or acaricides, and this problem has particularly become serious in recent years. When the same chemical is repeatedly applied to these pests, the controlling effect of the chemical on these pests inevitably decreases.

From a practical viewpoint, attempts have been made to solve the problem of pesticide resistance by avoiding the continuous application of the same chemical and applying different chemicals in proper order, or by using a mixture of chemicals having different actions and mechanisms. It has been particularly desired to develop new types of insecticides and acaricides.

In order to meet such a desire, the present inventors made extensive investigations, and have now found that certain novel 2,4-diphenyl-2-oxa- or thiazoline derivatives and 2-phenyl-4-benzyl-2-oxa- or thiazoline derivatives show very outstanding and particularly marked insecticidal and acaricidal activities with very low phytotoxicity on useful crops.

Thus, according to this invention, there is provided a compound represented by the following formula

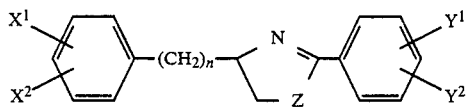

(I)

wherein
$X^1$ and $X^2$ are identical or different and each represents a hydrogen atom, a lower alkyl group, a lower alkoxy group, a halogen atom, a trifluoromethyl group or a trifluoromethoxy group;
$Y^1$ and $Y^2$ are identical or different and each represents a hydrogen atom, a lower alkyl group, a lower alkoxy group, a lower alkylthio group, a cyano group, a nitro group, a halogen atom or a trifluoromethyl group;
Z represents an oxygen or sulfur atom; and,
n is 0 or 1;
excepting the case where n is 0 and $X^1$ and $X^2$ are both hydrogen atoms, the case where n is 1 and $X^1$ and $X^2$ are members selected from the class consisting of hydrogen and halogen (excepting iodine) atoms, and the case where $Y^1$ and $Y^2$ are members selected from the class consisting of hydrogen and halogen (excepting iodine) atoms and nitro groups.

The term "lower", used in the present specification and the appended claims to qualify a group or a compound, means that the group or compound so qualified has not more than 6 carbon atoms.

The "lower alkyl group" may be a linear or branched alkyl group such as methyl, ethyl, n-propyl, isopropyl, n-butyl, isobutyl, sec-butyl, tert-butyl, n-pentyl, isoamyl, tert-pentyl, neopentyl or n-hexyl.

The "lower alkoxy group" and "lower alkylthio group" denote a (lower alkyl)-O- group and a (lower alkyl)-S-group respectively in which the lower alkyl moiety has the above meaning. Specific examples of these groups include methoxy, ethoxy, n-propoxy, isopropoxy, n-butoxy, isobutoxy, sec-butoxy, tert-butoxy, n-pentoxy and n-hexoxy; and methylthio, ethylthio, n-propylthio, isopropylthio, n-butylthio, isobutylthio, tert-butylthio and n-pentylthio.

The "halogen atom" includes fluorine, chlorine, bromine and iodine atoms.

Usually, n is preferably zero in formula (I) above.

Preferably, with regard to $X^1$ and $X^2$, (a) one of $X^1$ and $X^2$ represents a hydrogen atom, and the other represents a lower alkyl group, a lower alkoxy group, a fluorine atom, a chlorine atom, a trifluoromethyl group, or a trifluoromethoxy group, or (b) $X^1$ and $X^2$ being identical or different, each represent a lower alkyl group, a lower alkoxy group, a fluorine atom, a chlorine atom, a bromine atom or a trifluoromethyl group.

As regards $Y^1$ and $Y^2$, it is preferred that $Y^1$ and $Y^2$, being identical or different, each represent a lower alkyl group, a lower alkoxy group, a fluorine atom, a chlorine atom, a bromine atom, or a trifluoromethyl group.

Generally, Z is desirably an oxygen atom.

Especially preferred compounds of formula (I) are 2,4-diphenyl-2-oxazoline derivatives of the following formulae

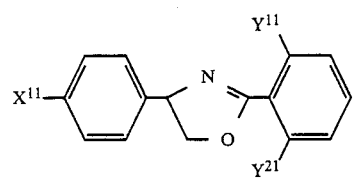

(I-1)

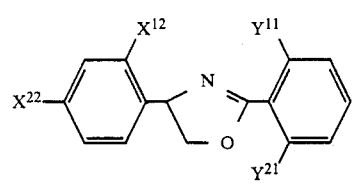

(I-2)

wherein $X^{11}$ represents a linear or branched lower alkyl group, a lower alkoxy group, a halogen atom, a trifluoromethyl group or a trifluoromethoxy group, and $X^{12}$, $X^{22}$, $Y^{11}$ and $Y^{21}$ each represent a halogen atom, particularly Cl or F.

The compound of formula (I) of this invention can be produced, for example, by reacting an aminoalcohol derivative represented by the following formula

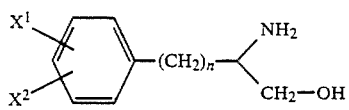

wherein $X^1$, $X^2$ and n are as defined above, with a benzoic acid derivative represented by the following formula

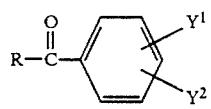

wherein R represents a hydroxyl group or a halogen atom, and $Y^1$ and $Y^2$ are as defined above,
in the presence of a dehydrating agent and, if required, a base.

When the reaction of the compound of formula (II) with the compound of formula (III) is carried out at a relatively high temperature, for example, at a temperature of about 70° C. to the refluxing temperature of the solvent, preferably at a temperature of 100 to 140° C., the compound of formula (I) can be produced in one step.

Preferably, this reaction is carried out usually in a solvent. The solvent may be, for example, an aromatic hydrocarbon such as benzene, toluene or xylene or a halogenated aromatic hydrocarbon such as chlorobenzene or diclorobenzene. The dehydrating agent may be, for example, sulfuric acid, thionyl chloride, phosphorus oxychloride, phosphorus pentoxide or phosphorus pentasulfide. The use of sulfuric acid, thionyl chloride, phosphorus oxychloride or phosphorus pentoxide gives a compound of formula (I) in which Z is an oxygen atom, and the use of phosphorus pentasulfide gives a compound of formula (I) in which Z represents a sulfur atom. Desirably, the dehydrating agent is used generally in an amount of 1 to 5 moles, preferably 1.5 to 3 moles, per mole of the compound of formula (II).

When a compound of formula (III) in which R is a hydroxyl group is used as a starting material in the above reaction, it is not particularly necessary to use a base. However, when a compound of formula (III) in which R represents a halogen atom is used, the reaction is preferably carried out in the presence of a base. Examples of usable bases are inorganic bases such as sodium hydroxide, potassium hydroxide, potassium carbonate, sodium carbonate, and sodium hydrogen carbonate, and organic bases such as triethylamine, N,N-dimethylaniline, pyridine and 4-N,N-dimethylaminopyridine. The amount of the base used is not strictly limited. Usually, its suitable amount is 1 to 3 equivalents, preferably 1.2 to 2 moles, per mole of the compound of formula (III).

The proportion of the compound of formula (III) relative to the compound of formula (II) is not critical and may be varied over a wide range. Generally, it is convenient to use the compound of formula (III) in an amount of 1 to 3 moles, especially 1 to 1.5 moles, per mole of the compound of formula (II).

When a compound of formula (III) in which R is a halogen atom is used as the starting material and the reaction is carried out in the presence of the base at a relatively low temperature, for example about 0 to 50° C., preferably 5 to 20° C., a compound represented by the following formula

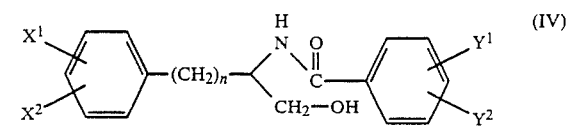

wherein $X^1$, $X^2$, $Y^1$, $Y^2$ and n are as defined above,
is formed as an intermediate. Cyclization of the compound of formula (IV) in the presence of a dehydrating agent can also give the compound of formula (I).

The reaction of the compound of formula (II) with the acid halide of formula (III) may usually be carried out in a solvent. The solvent may be, for example, water; an alcohol such as methanol and ethanol; an ether such as diethyl ether, tetrahydrofuran, dioxane and diglyme; an aromatic hydrocarbon such as benzene, toluene and xylene; or a halogenated hydrocarbon such as dichloromethane, dichloroethane, chloroform and carbon tetrachloride.

The intermediate compound of formula (IV) may be isolated, or may be directly subjected to the next cyclizing reaction without isolation. Examples of the dehydrating agent used in this cyclization reaction are as given above. If sulfuric acid, thionyl chloride, phosphorus oxychloride or phosphorus pentoxide is used, a compound of formula (I) in which Z is an oxygen atom is obtained. If phosphorus pentasulfide is used, a compound of formula (I) in which Z is a sulfur atom is obtained. The dehydrating agent may be used generally in an amount of 0.5 to 2 moles, preferably 0.8 to 1.5 moles, per mole of the compound of formula (IV).

The cyclization reaction may be carried out in the aromatic hydrocarbon solvent or the halogenated aromatic hydrocarbon solvent at a temperature of generally about 70° C. to the refluxing temperature of the solvent, preferably at a temperature of 100 to 140° C.

The compound of formula (I) in which Z is an oxygen atom may also be produced by reacting the compound of formula (IV) with a halogenating agent and treating the resulting compound of formula

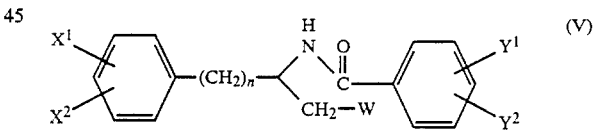

wherein W represents a halogen atom, and $X^1$, $X^2$, $Y^1$, $Y^2$ and n are as defined above,
with a base to cyclize it.

Examples of the halogenating agent used for halogenating the compound of formula (IV) are thionyl chloride, phosphorus oxychloride, phopsphorus trichloride and phosphorus tribromide. Generally, it is used in an amount of 1 to 3 moles, preferably 1.2 to 2 moles, per mole of the compound of formula (IV).

The halogenation of the compound of formula (IV) may be carried out in a solvent, preferably the aromatic hydrocarbon or halogenated hydrocarbon mentioned hereinabove. The reaction temperature is generally about 0 to 120° C., preferably 20 to 70° C.

The compound of formula (V) may be subjected to the cyclization reaction with or without prior isolation. Usually, it is preferred to carry out the cyclization reaction in the presence of an alcohol such as methanol or ethanol, and the inorganic base mentioned above. The suitable amount of the base is generally 1 to 3 equivalents, preferably 1.2 to 2 equivalents, per mole of the compound of formula (V).

The cyclization reaction temperature that can be employed conveniently is generally about 50 to 100° C., preferably 60 to 80° C.

The resulting compound of formula (I) may be isolated and purified by known methods, for example column chromatography and recrystallization.

Benzene, methanol, ethanol, chloroform, nhexane, ethyl acetate, or mixtures thereof may be used as a solvent for column chromatography or recrystallization.

The production of the compound of formula (I) will be specifically described by the following examples.

SYNTHESIS EXAMPLE 1

Synthesis of 2-(2-chlorophenyl)-4-(2-chlorophenyl)-2-oxazoline:

A solution of 1.75 g (10 millimoles) of 2-chlorobenzoyl chloride in 15 ml of tetrahydrofuran was added over 30 minutes with ice cooling and stirring to a 100 ml eggplant-shaped flask containing 1.72 g (10 millimoles) of 2-amino-2-(2-chlorophenyl)-ethanol, 1.01 g (10 millimoles) of triethylamine and 30 ml of tetrahydrofuran. The mixture was further stirred at 20° C. for 3 hours, and the triethylamine hydrochloride formed was removed by a glass filter. The filtrate was concentrated under reduced pressure.

Thionyl chloride (5 ml; 68 millimoles) was added all at once to a 100 ml eggplant-shaped flask containing the concentrate and 30 ml of benzene, and the mixture was refluxed for 3 hours with stirring. The reaction mixture was cooled to room temperature, and concentrated under reduced pressure. The concentrate was dissolved in 100 ml of ethyl acetate, washed with a saturated aqueous solution of sodium hydrogen carbonate, dried over anhydrous sodium sulfate, and then concentrated under reduced pressure. A 100 ml eggplant-shaped flask containing this concentrate and 30 ml of ethanol was heated to 70° C. over an oil bath with stirring, and then 15 ml of a 3 % aqueous solution of sodium hydroxide was added over 10 minutes. The mixture was further stirred at 70° C. for 20 minutes, and concentrated under reduced pressure. Benzene (100 ml) was added to the concentrate, and the mixture was washed with a saturated aqueous solution of sodium chloride, dried over anhydrous sodium sulfate, and concentrated under reduced pressure. The concentrate was purified by silica gel column chromatography (mobile phase: hexane/ethyl acetate=7/3) to give 2-(2-chlorophenyl)-4-(2-chlorophenyl)-2-oxazoline (compound No. 12) as a yellow viscous oil. Yield 1.1 g (42.7 %).

|  | Elemental analysis values | | |
| --- | --- | --- | --- |
|  | C | H | N |
| Found: | 60.87% | 3.71% | 4.88% |
| Calculated: | 61.66% | 3.80% | 4.79% |

NMR spectrum (internal standard TMS; solvent CDCl$_3$):δppm 4.13 (t, J=8 Hz, 1 H), 4.97 (t, J=8 Hz, 1 H), 5.88 (dd, J$_1$=8 Hz, J$_2$=8 Hz, 1 H), 7.1–8.1 (m, 8 H).

Infrared absorption spectrum (sodium chloride plate): ν(cm$^{-1}$):

2,900–3,050 (CH), 1,650 (C=N).

SYNTHESIS EXAMPLE 2

Synthesis of 2-(2-chloro-6-fluorophenyl)-4-(4-t-butylphenyl)-2-oxazoline:

A 100 ml eggplant-shaped flask was charged with 1.4 g (7.25 millimoles) of 2-amino-2-(4-t-butylphenyl)-1-ethanol and 0.73 g (7.25 millimoles) of triethylamine and 30 ml of tetrahydrofuran, and a solution of 1.4 g (7.25 millimoles) of 2-chloro-6-fluorobenzoyl chloride in 10 ml of tetrahydrofuran was added over 30 minutes to the flask with ice cooling and stirring. The mixture was stirred further for 3 hours at room temperature. The resulting triethylamine hydrochloride was removed by a glass filter, and the filtrate was concentrated under reduced pressure. The concentrate, thionylchloride (2.6 g; 21.8 and 50 ml of benzene were put in a 200 ml eggplant-shaped flask, and refluxed for 5 hours. The reaction mixture was concentrated under reduced pressure. Fifty milliliters of methanol was added to the remaining oil, and the mixture was heated to 60° C. To the mixture was added dropwise 5 ml of a 15 % aqueous solution of sodium hydroxide. After the addition, the mixture was stirred at the same temperature for 1 hour, transferred into water, and extracted with ethyl acetate. The extract was purified by silica gel column chromatography (mobile phase: hexane/ethyl acetate=8/2) to give 2-(2-chloro-6-fluorophenyl)-4-(4-t-butylphenyl)-2-oxazoline (compound No. 45) as a colorless oil. Yield 1.8 g (74.9 %).

|  | Elemental analysis values | | |
| --- | --- | --- | --- |
|  | C | H | N |
| Found: | 68.65% | 5.81% | 4.16% |
| Calculated: | 68.77% | 5.77% | 4.22% |

NMR Spectrum (internal standard TMS; solvent CDCl$_3$): δppm 1.33 (s, 9 H), 4.30 (t, J=9 Hz, 1 H), 4.80 (t, J=8 Hz, 1 H), 5.48 (dd), J$_1$=8 Hz, J$_2$=9 Hz, 1 H), 6.9–7.8 (m, 7 H).

Infrared absorption spectrum (sodium chloride plate): ν(cm$^{-1}$):

2,860–3,100 (CH), 1,676 (C=N)

SYNTHESIS EXAMPLE 3

Synthesis of 2-(3-chlorophenyl)-4-(4-methyl-benzyl)-2-oxazoline:

A solution of 1.75 g (10 millimoles) of 3-chlorobenzoyl chloride in 15 ml of tetrahydrofuran was added with ice cooling and stirring to a 100 ml egg-plant-shaped flask containing 1.61 g (10 millimoles) of 2-amino-3-(4-methyl-phenyl)-1-propanol, 1.01 g (10 millimoles) of triethylamine and 30 ml of tetrahydrofuran over the course of 30 minutes. The mixture was further stirred at 20° C. for 3 hours. The resulting triethylamine hydrochloride was removed by a glass filter, and the filtrate was concentrated under reduced pressure. Thionyl chloride (5 ml; 68 millimoles) was added all at once to a 100 ml eggplant-shaped flask containing this concentrate and 30 ml of benzene. With stirring, the mixture was refluxed for 3 hours. The reaction mixture was cooled to room temperature, and concentrated under reduced pressure. The concentrate was dissolved in 100 ml of ethyl acetate, washed with a saturated aqueous solution of sodium hydrogen carbonate, dried over anhydrous sodium sulfate, and concentrated under reduced pressure. A 100 ml eggplant-shaped flask containing this concentrate and 30 ml of ethanol was heated to 70° C. over an oil bath with stirring, and 15 ml of a 3 % aqueous solution of sodium hydroxide was added over 10 minutes. The mixture was further stirred at 70° C. for 20 minutes, and concentrated under reduced pressure. Benzene (100 ml) was added to the concentrate, and the mixture was washed with a saturated aqueous solution of sodium chloride, dried over anhydrous sodium sulfate, and concentrated under reduced pressure. The concentrate was purified by silica gel column chromatography (mobile phase: hexane/ethyl acetate=7/3) to give 2-(3-chlorophenyl)-4-(4-methylbenzyl) -2-oxazoline (compound No. 108) as a yellow viscous oil. Yield 1.7 g (59.5 %).

|  | Elemental analysis values | | |
| --- | --- | --- | --- |
|  | C | H | N |
| Found: | 70.86% | 5.41% | 5.01% |
| Calculated: | 71.45% | 5.64% | 4.90% |

NMR spectrum (internal standard TMS; solvent CDCl₃): δppm
2.33 (s, 3 H), 2.6–3.5 (m, 2 H), 4.0–4.9 (m, 3 H), 7.0–7.9 (m, 8 H).
Infrared absorption spectrum (sodium chloride plate): ν(cm⁻¹):
2,850–3,100 (CH), 1,654 (C=N).

SYNTHESIS EXAMPLE 4

Synthesis of 2-(2-methoxyphenyl)-4-phenyl-2-thiazoline:

A solution of 1.71 g (10 millimoles) of 2-methoxybenzoyl chloride in 15 ml of tetrahydrofuran was added with ice cooling and stirring to a 100 ml egg-plant-shaped flask containing 1.37 g (10 millimoles) of 2-amino-2-phenyl-ethanol, 1.01 g (10 millimoles) of triethylamine and 30 ml of tetrahydrofuran over the course of 30 minutes. The mixture was further stirred at 20° C. for 3 hours. The resulting triethylamine hydrochloride was removed by a glass filter, and the filtrate was concentrated under reduced pressure.

A 100 ml eggplant-shaped flask containing the resulting concentrate, 1.78 g (8 millimoles) of phosphorus pentasulfide and 30 ml of toluene was subjected to refluxing for 16 hours. The reaction mixture was cooled to 20° C. A 30 % aqueous solution of sodium hydroxide (20 ml) was added, and the organic layer was separated. The organic layer was washed with a saturated aqueous solution of sodium chloride, dried over anhydrous sodium sulfate, and concentrated under reduced pressure. The concentrate was purified by silica 9el column chromatography (mobile phase: hexane/ethyl acetate=8/2) to give 2-(2-methoxyphenyl)-4-phenyl-2-thiazoline (compound No. 110) as yellow crystals. Yield 2.1 9 (77.8 %).

|  | C | H | N |
| --- | --- | --- | --- |
| Found: | 71.03% | 5.49% | 4.98% |
| Calculated: | 71.31% | 5.61% | 5.20% |

NMR spectrum (internal standard TMS; solvent CDCl₃): δppm
3.1–4.0 (m, 2 H) 3.95 (s, 3 H), 5.70 (t, J=9 Hz, 1 H), 7.0–8.2 (m, 9 H).
Infrared absorption spectrum (sodium chloride plate): ν(cm⁻¹):
2,850–3,100 (CH), 1,594 (C=N).

The compounds indicated in Table 1 were synthesized in the same way as in Synthesis Examples 1 to 4. Table 1 also describes the compounds obtained in Synthesis Examples 1 to 4.

TABLE 1

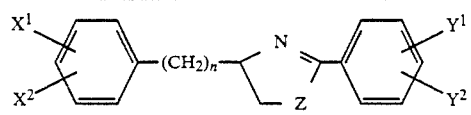

| Compound No. | Z | n | X¹ | X² | Y¹ | Y² | Physical constant (ND²⁵ or melting point) |
| --- | --- | --- | --- | --- | --- | --- | --- |
| 1 | O | 0 | H | H | 2-I | H | 1.6244 |
| 2 | O | 0 | H | H | 2-CF₃ | H | 1.5427 |
| 3 | O | 0 | H | H | 2-CH₃ | H | 1.5949 |
| 4 | O | 0 | H | H | 2-O—CH₃ | H | 1.6008 |
| 5 | O | 0 | H | H | 2-O—C₂H₅ | H | 1.5529 |
| 6 | O | 0 | H | H | 2-S—CH₃ | H | 88.0–89.5° C. |
| 7 | O | 0 | H | H | 2-S—C₂H₅ | H | 91.0–92.5° C. |
| 8 | O | 0 | H | H | 4-CN | H | 95,0–97.0° C. |
| 9 | O | 0 | H | H | 2-Cl | 5-CF₃ | 1.5484 |
| 10 | O | 0 | 2-F | H | 2-Cl | H | 1.5855 |
| 11 | O | 0 | 2-Cl | H | 2-F | H | 1.5631 |
| 12 | O | 0 | 2-Cl | H | 2-Cl | H | 1.6093 |
| 13 | O | 0 | 2-Cl | H | 2-Br | H | 53.0–55.0° C. |
| 14 | O | 0 | 2-Cl | H | 3-Cl | H | 75.0–76.0° C. |
| 15 | O | 0 | 2-Br | H | 2-F | H | 1.6067 |
| 16 | O | 0 | 2-Br | H | 2-Cl | H | 1.6213 |
| 17 | O | 0 | 2-Br | H | 2-Br | H | 1.6324 |
| 18 | O | 0 | 3-Cl | H | 2-Cl | H | 1.6093 |
| 19 | O | 0 | 3-Cl | H | 2-Br | H | 1.6075 |
| 20 | O | 0 | 3-Cl | H | 4-Cl | H | 1.6105 |
| 21 | O | 0 | 4-Br | H | 2-Cl | H | 1.6176 |
| 22 | O | 0 | 4-Cl | H | H | H | 70.5–71.5° C. |
| 23 | O | 0 | 4-Cl | H | 2-Cl | H | 1.6075 |
| 24 | O | 0 | 4-Cl | H | 3-Cl | H | 1.6080 |
| 25 | O | 0 | 4-Cl | H | 4-Cl | H | 89.0–92.5° C. |
| 26 | O | 0 | 4-Cl | H | 2-Br | H | 1.6072 |

TABLE 1-continued

Structure: X¹, X² on left phenyl ring; -(CH₂)ₙ-CH-N=CH- linkage with Z on the CH-CH₂ bridge; Y¹, Y² on right phenyl ring.

| Compound No. | Z | n | X¹ | X² | Y¹ | Y² | Physical constant ($N_D^{25}$ or melting point) |
|---|---|---|---|---|---|---|---|
| 27 | O | 0 | 4-F | H | 2-Cl | H | 1.5878 |
| 28 | O | 0 | 4-CF₃ | H | 2-Cl | H | 1.5519 |
| 29 | O | 0 | 4-CH₃ | H | 2-Cl | H | 1.5962 |
| 30 | O | 0 | 4-OCH₃ | H | 2-Cl | H | 1.5906 |
| 31 | O | 0 | 2-Cl | H | 2-F | 6-F | 52.0–53.5° C. |
| 32 | O | 0 | 4-Cl | H | 2-F | 4-F | 1.5760 |
| 33 | O | 0 | 4-Cl | H | 2-F | 6-F | 1.5701 |
| 34 | O | 0 | 4-Cl | H | 2-Cl | 6-F | 1.5814 |
| 35 | O | 0 | 4-Cl | H | 2-CH₃ | 4-Cl | 45.0–47.0° C. |
| 36 | O | 0 | 4-Cl | H | 2-Cl | 6-Cl | 53.5–55.5° C. |
| 37 | O | 0 | 4-Cl | H | 2-Cl | 4-NO₂ | 1.6212 |
| 38 | O | 0 | 4-F | H | 2-Cl | 6-F | 1.5654 |
| 39 | O | 0 | 4-F | H | 2-Cl | 4-NO₂ | 1.6176 |
| 40 | O | 0 | 4-Br | H | 2-Cl | 6-F | 1.5944 |
| 41 | O | 0 | 4-Br | H | 2-F | 6-F | 67.5–69.0° C. |
| 42 | O | 0 | 4-CH₃ | H | 2-F | 6-F | 1.5552 |
| 43 | O | 0 | 4-OC₂H₅ | H | 2-F | 6-F | 1.5578 |
| 44 | O | 0 | 4-t-C₄H₉ | H | 2-F | 6-F | 1.5471 |
| 45 | O | 0 | 4-t-C₄H₉ | H | 2-Cl | 6-F | 1.5592 |
| 46 | O | 0 | 4-t-C₅H₁₁ | H | 2-F | 6-F | 1.5459 |
| 47 | O | 0 | 4-t-C₅H₁₁ | H | 2-Cl | 6-F | 1.5581 |
| 48 | O | 0 | 4-n-C₅H₁₁ | H | 2-F | 6-F | 1.5396 |
| 49 | O | 0 | 4-n-C₅H₁₁ | H | 2-Cl | 6-F | 1.5519 |
| 50 | O | 0 | 4-Neo-C₅H₁₁ | H | 2-F | 6-F | 1.5394 |
| 51 | O | 0 | 4-Neo-C₅H₁₁ | H | 2-Cl | 6-F | 1.5496 |
| 52 | O | 0 | 4-n-C₆H₁₃ | H | 2-F | 6-F | 1.5357 |
| 53 | O | 0 | 4-n-C₆H₁₃ | H | 2-Cl | 6-F | 1.5469 |
| 54 | O | 0 | 4-O-n-C₅H₁₁ | H | 2-F | 6-F | 1.5348 |
| 55 | O | 0 | 4-O-n-C₅H₁₁ | H | 2-Cl | 6-F | 1.5433 |
| 56 | O | 0 | 4-O-i-C₅H₁₁ | H | 2-F | 6-F | 1.5357 |
| 57 | O | 0 | 4-O-i-C₅H₁₁ | H | 2-Cl | 6-F | 1.5495 |
| 58 | O | 0 | 4-O-n-C₆H₁₃ | H | 2-F | 6-F | 1.5342 |
| 59 | O | 0 | 4-O-n-C₆H₁₃ | H | 2-Cl | 6-F | 1.5392 |
| 60 | O | 0 | 4-t-C₄H₉ | H | 2-CH₃ | 6-CH₃ | 1.5589 |
| 61 | O | 0 | 4-O—C₂H₅ | H | 2-Cl | 6-F | 1.5708 |
| 62 | O | 0 | 4-O-i-C₃H₇ | H | 2-F | 6-F | 1.5504 |
| 63 | O | 0 | 4-O-i-C₃H₇ | H | 2-Cl | 6-F | 1.5635 |
| 64 | O | 0 | 4-O-n-C₄H₉ | H | 2-F | 6-F | 60.5–62.5° C. |
| 65 | O | 0 | 4-CF₃ | H | 2-Cl | 6-F | 104.0–105.5° C. |
| 66 | O | 0 | 4-CF₃ | H | 2-F | 4-F | 1.5296 |
| 67 | O | 0 | 4-CF₃ | H | 2-F | 6-F | 51.0–53.0° C. |
| 68 | O | 0 | 4-O—CF₃ | H | 2-Cl | 6-Cl | 69.5–70.0° C. |
| 69 | O | 0 | 4-O—CF₃ | H | 2-Cl | 6-F | 1.5216 |
| 70 | O | 0 | 4-O—CF₃ | H | 2-F | 6-F | 1.5085 |
| 71 | O | 0 | 2-Cl | 4-Cl | 2-Cl | H | 1.6080 |
| 72 | O | 0 | 3-Cl | 4-Cl | 2-Cl | 6-F | 50.0–52.0° C. |
| 73 | O | 0 | 2-Cl | 4-Cl | 2-Cl | 6-F | 1.5979 |
| 74 | O | 0 | 2-Cl | 4-CF₃ | 2-Cl | 6-F | 1.5935 |
| 75 | O | 0 | 2-Cl | 3-Cl | 2-Cl | 6-F | 70.0–74.5° C. |
| 76 | O | 0 | 2-Cl | 4-Cl | 2-F | 6-F | 49.0–50.0° C. |
| 77 | O | 0 | 2-Cl | 4-F | 2-F | 6-F | 1.6089 |
| 78 | O | 0 | 2-Cl | 4-F | 2-Cl | 6-F | 1.6102 |
| 79 | O | 0 | 2-F | 4-F | 2-F | 6-F | 1.5398 |
| 80 | O | 0 | 2-F | 4-Cl | 2-F | 6-F | 65.0–67.0° C. |
| 81 | O | 0 | 2-F | 4-Cl | 2-Cl | 6-F | 1.5864 |
| 82 | O | 0 | 2-F | 4-F | 2-Cl | 6-F | 1.5543 |
| 83 | O | 0 | 2-CF₃ | 4-Cl | 2-Cl | 6-F | 1.5947 |
| 84 | O | 0 | 2-CH₃ | 4-Cl | 2-F | 6-F | 1.5656 |
| 85 | O | 0 | 2-CH₃ | 4-Cl | 2-Cl | 6-F | 1.5768 |
| 86 | O | 0 | 2-CH₃ | 4-Cl | 2-Cl | 6-Cl | 1.5854 |
| 87 | O | 0 | 3-Cl | 4-Cl | 2-F | 6-F | 82.0–83.0° C. |
| 88 | O | 0 | 3-Cl | 5-Cl | 2-F | 6-F | 1.5734 |
| 89 | O | 0 | 3-Cl | 5-Cl | 2-Cl | 6-F | 1.5854 |
| 90 | O | 0 | 3-Cl | 4-F | 2-F | 6-F | 68.0–69.0° C. |
| 91 | O | 0 | 3-Cl | 4-F | 2-Cl | 6-F | 51.0–52.5° C. |
| 92 | O | 0 | 3-Cl | 4-CH₃ | 2-F | 6-F | 1.5672 |
| 93 | O | 0 | 3-Cl | 4-C₂H₅ | 2-Cl | 6-F | 83.0–85.0° C. |
| 94 | O | 0 | 3-Cl | 4-O—C₂H₅ | 2-F | 6-F | 73.0–75.0° C. |
| 95 | O | 0 | 3-F | 4-Cl | 2-F | 6-F | 1.5641 |
| 96 | O | 0 | 3-F | 4-Cl | 2-Cl | 6-F | 1.5755 |
| 97 | O | 0 | 3-F | 5-F | 2-F | 6-F | 30.0–31.5° C. |
| 98 | O | 0 | 3-F | 5-F | 2-Cl | 6-F | 1.5475 |
| 99 | O | 0 | 3-F | 5-F | 2-Cl | 6-Cl | 1.5682 |
| 100 | O | 0 | 3-Br | 4-O—C₂H₅ | 2-Cl | 6-Cl | 63.0–66.0° C. |

TABLE 1-continued $$X^1, X^2 \text{-phenyl-}(CH_2)_n\text{-CH(Z)-N=CH-phenyl-}Y^1, Y^2$$

| Compound No. | Z | n | $X^1$ | $X^2$ | $Y^1$ | $Y^2$ | Physical constant ($N_D^{25}$ or melting point) |
|---|---|---|---|---|---|---|---|
| 101 | O | 0 | 3-Br | 4-O—CH$_3$ | 2-Cl | 6-F | 1.5877 |
| 102 | O | 1 | H | H | 2-CF$_3$ | H | 1.5366 |
| 103 | O | 1 | H | H | 3-CH$_3$ | H | 1.5811 |
| 104 | O | 1 | H | H | 2-O—CH$_3$ | H | 1.5912 |
| 105 | O | 1 | H | H | 3-CF$_3$ | H | 30.0–32.0° C. |
| 106 | O | 1 | H | H | 3-CH$_3$ | H | 1.5751 |
| 107 | O | 1 | H | H | 4-CH$_3$ | H | 1.5862 |
| 108 | O | 1 | 4-CH$_3$ | H | 3-Cl | H | 64.0–65.5° C. |
| 109 | S | 0 | H | H | 2-CH$_3$ | H | 1.6332 |
| 110 | S | 0 | H | H | 2-O—CH$_3$ | H | 52.0–54.0° C. |
| 111 | S | 0 | H | H | 2-O—C$_2$H$_5$ | H | 1.6259 |
| 112 | S | 0 | 2-Cl | H | 3-Cl | H | 1.6442 |
| 113 | S | 0 | 3-Cl | H | 3-Cl | H | 1.6467 |
| 114 | S | 0 | 4-O—C$_2$H$_5$ | H | H | H | 1.6218 |
| 115 | S | 0 | 4-O—CH$_3$ | H | H | H | 1.6247 |
| 116 | S | 0 | 4-O—C$_2$H$_5$ | H | H | H | 1.6275 |
| 117 | S | 0 | 4-CF$_3$ | H | 2-Cl | 6-F | 1.5634 |
| 118 | S | 1 | H | H | 2-CF$_3$ | H | 1.5637 |
| 119 | S | 1 | H | H | 2-CH$_3$ | H | 1.6142 |
| 120 | S | 1 | H | H | 2-O—CH$_3$ | H | 1.6307 |
| 121 | S | 1 | H | H | 2-O—C$_2$H$_5$ | H | 1.6100 |
| 122 | S | 1 | H | H | 2-O-n-C$_3$H$_7$ | H | 1.6036 |
| 123 | S | 1 | H | H | 2-O-n-C$_4$H$_9$ | H | 1.5944 |
| 124 | S | 1 | H | H | 2-S—CH$_3$ | H | 63.0–64.0° C. |
| 125 | S | 1 | H | H | 3-O—CH$_3$ | H | 1.6167 |
| 126 | S | 1 | H | H | 4-C$_2$H$_5$ | H | 1.6071 |
| 127 | S | 1 | H | H | 4-O—CH$_3$ | H | 87.0–90.0° C. |
| 128 | S | 1 | 2-Cl | H | 2-O—CH$_3$ | H | 1.6286 |
| 129 | S | 1 | 3-Cl | H | 2-O—CH$_3$ | H | 1.6302 |
| 130 | S | 1 | 4-CH$_3$ | H | 2-Cl | H | 1.6127 |
| 131 | S | 1 | 4-CH$_3$ | H | 2-O—CH$_3$ | H | 1.6200 |

The compounds of formula (I) provided by this invention, as seen from Test Examples given hereinafter, show strong ovicidal and pesticidal activities against insects and mites noxious to agriculture and horticulture, and have little phytotoxicity to useful crops. Accordingly, they are useful as active ingredients of agricultural-horticultural insecticides and acaricides. The compounds of this invention can be expected to exhibit an excellent control efficacy against insects and mites which do damage to useful crops. These pests include aphids such as *Myzus persicae, Alphis gossypii, Lipaphis erysimi, Aphis citricola* and *Nippolachnus piri;* planthoppers and leafhoppers such as *Nephotettix cincticeps, Laodelphax striatellus, Soqatella furcifera* and *Nilaparvata lugens;* and mites such as *Tetranychus urticae, Tetranychus cinnabarinus, Tetranychus kanzawai, Panonychus ulmi* and *Panonychus citri.*

For use as an active ingredient of an insecticide and acaricide, one or more compounds of formula (I) may be used as such, or usually as various formulations in admixture with agronomically acceptable adjuvants.

Carriers, emulsifiers, dispersants and stabilizers may be cited as adjuvants that can be used in formulation.

The carriers include solid and liquid carriers. Examples of the solid carriers are powders of minerals such as diatomaceous earth, talc, clay, alumina, kaolin, montmorillonite, silicates and white carbons; and powders of animal or vegetable materials such as starch, soybean meal, wheat flour and fish meal. Examples of the liquid carriers are water; alcohols such as methanol and ethylene glycol; ketones such as acetone and methyl ethyl ketone; ethers such as dioxane and tetrahydrofuran; aliphatic hydrocarbons such as kerosene and lamp oil; aromatic hydrocarbons such as xylene, trimethylbenzene, tetramethylbenzene, cyclohexane and solvent naphtha; halogenated hydrocarbons such as chloroform and chlorobenzene; acid amides such as dimethylformamide; esters such as ethyl acetate; nitriles such as acetonitrile; and sulfur-containing compounds such as dimethyl sulfoxide.

Examples of the emulsifiers include non-ionic emulsifiers such as polyoxyalkylene alkyl ethers, polyoxyalkylene alkylaryl ethers, polyoxyalkylene fatty acid esters and polyoxyalkylene sorbitan fatty acid esters; anionic emulsifiers such as alkylaryl sulfuric ester salts and polyoxyalkylene alkylaryl sulfuric acid esters, and mixtures of these.

Examples of the dispersants include ethylene glycol, glycerol, ligninsulfonic acid salts, methyl cellulose, alkylsulfuric acid ester salts, alkyl-benzenesulfonic acid salts, dialkylsulfosuccinic acid ester salts, naphthalenesulfonic acid-formaldehyde condensate, polyoxyalkylene alkylsulfuric acid ester salts, and mixtures of these.

Examples of the stabilizers include phosphoric acid esters, epichlorohydrin, phenyl glycidyl ether, glycols, nonionic surface-active agents, and aromatic diamines.

The formulation containing the compound of formula (I) provided by this invention may, as required, contain other agricultural chemicals such as other insecticides, other acaricides, fungicides and attractants to produce a higher efficacy.

Examples of such other insecticides and acaricides include organophosphate compounds such as Fenitrothion (0,0-dimethyl 0-4-nitro-m-tolyl phosphorothioate), Diazinon (0,0-diethyl 0-2-isopropyl-6-methyl-pyrimidin-4-yl phosphorothioate), Chlorpyrifos-methyl

[O,O-dimethyl 0-(3,5,6-trichloro-2-pyridyl)phosphorothioate] and Acephate (O,S-dimethylacetyl phosphoroamidothioate); carbamate compounds such as Carbaryl (1-naphthylmethyl carbamate), Carbofuran (2,3-dihydro-2,2-dimethylbenzofuran-7-yl-methylcarbamate) and Methomyl [S-methyl N-(methylcarbamoyloxy)thioacetoimidate]; organochlorine compounds such as Dicofol [2,2,2-trichloro-1,1-bis(4-chlorophenyl)ethanol]; organometallic compounds such as Fenbutatin oxide [hexakis(beta,beta-dimethylphenethyl)distannoxane]; pyrethroid compounds such as Fenvalerate (RS)-alpha-cyano-3-phenoxybenzyl (RS)-2-(4-chlorophenyl)-3-methylbutyrate)] and Permethrin 3-phenoxybenzyl (IRS)cis,trans -3-(2,2-dichlorovinyl)-2,2-dimethylcyclopropane carboxylate); benzoylurea compounds such as Diflubenzuron [1-(4-chlorophenyl)-3-(2,6-difluorobenzoyl)urea] and Chlorfluazuron 1-(3,5-dichloro-4-(3-chloro-5-trifluoromethyl-2-pyridyloxy)phenyl)-3-(2,6-difluorobenzoyl)urea]; and other compounds such as Buprofezin (2-t-butylimino-3-isopropyl-5-phenyl-3,4,5,6-tetra -hydro-2H-1,3,5-thiadiazin-4-one) and Hexythiazox [trans-5-(4-chlorophenyl)-N-cyclohexyl-4-methyl-2-oxothiazolidinone-3-carboxamide).

Examples of the fungicides include organophosphorus compounds such as Iprobenfos (S-benzyl O,O-diisopropylphosphorothioate) and Edifenphos (0-ethyl S,S-diphenylphosphorodithioate); organochlorine compounds such as Phthalide (4,5,6,7-tetrachlorophthalide); dithiocarbamate compounds such as a polymer of Zineb [zinc ethylenebis(dithiocarbamate)]and Polycarbamate [dizincbis(dimethyldithiocarbamate)]; N-halogenothioalkyl compounds such as Captan 3a,4,7,7a-tetrahydro-N-(trichloromethanesulfenyl)phthalimide] and Captafol [3a,4,7,7a-tetrahydro-N-(1,1,2,2-tetrachloroethanesulfenyl)phthalimide]; dicarboximide compounds such as Glycophene 3-(3,5-dichlorophenyl)-N-isopropyl-2,4-dioxoimidazolidin-1-carboxamide], Vinclozolin (RS)-3-(3,5-dichlorophenyl) -5-methyl-5-vinyl-1,3-oxazolidin-2,4-dione] and Procymidox N-(3,5-diclorophenyl)-1,2-dimethylcyclopropane-1,2-dicarboximide]; benzimidazole compounds such as Benomyl methyl 1-(butylcarbamoyl)benzimidazole-2-yl carbamate); azole compounds such as Bitertanol 1-(biphenyl-4-yloxy)-3,3-dimethyl-1-(1H-1,2,4-triazol-1-yl)butan-2-ol] and Triflumizole [1-(N-(4-chloro-2-trifluoromethylphenyl)-2-propoxyacetimidoyl)imidazole); and benzanilide compounds such as Mepronil (3-isopropoxy-0-toluanilide) and Flutolanil (alpha,alpha,alpha-trifluoro-3-isopropoxy-0-toluanilide).

Illustrative of the attractant are benzoic acid, 4-allyl-2-methoxyphenol and 4-(p-acetoxyphenyl)-2-butanone.

The compound (I) of this invention may be formulated into a wettable powder, granules, a dust, a pulverulent composition, an emulsifiable concentrate, a sol, etc. together with the above-described adjuvants by methods known in the field of preparing agricultural chemicals.

The proportion of the active compound of formula (I) in these formulations may be varied widely depending upon the type of the compound (I), the type of formulation, etc. Generally, its suitable proportion is 0.01 to 80 % by weight, and the preferred proportion of the compound of formula (I) may be 0.01 to 50 % by weight, especially preferably 0.1 to 20 % by weight, for a liquid preparation, an emulsifiable concentrate and a wettable powder, and 0.01 to 20 % by weight, especially preferably 0.1 to 10 % by weight, for a dust, a pulverulent composition and granules.

The formulation containing the compound (I) of the invention may be used to control noxious insects and/or mites by applying it directly to insects or mites noxious to agricultural and horticultural crops, or to their habitat.

The rate of the compound of formula (I) to be applied at this time may be properly varied depending upon the type of the active compound, the type of the formulation, the state of occurrence of the pests, etc. It may be applied generally at a rate of 1 to 10,000 g/hectare, preferably 10 to 1,000 g/hectare. Specifically, in the case of the emulsifiable concentrate, liquid preparation and wettable powder, they are usually diluted to 1,000 to 10,000 times, and can be applied at a rate of 1,000 to 10,000 liters per hectare. In the case of the dust, pulverulent composition and granules, they may be applied at a rate of 2 to 40 kg per hectare.

Formulation examples are given below to illustrate the formulation of the compound of formula (I) provided by the invention. All parts in these examples are by weight.

FORMULATION EXAMPLE 1

Emulsifiable concentrate

Xylene (67 parts) are added to 20 parts of compound No. 45 of the invention, 3 parts of alkylaryl sulfonate and 10 parts of polyoxyalkylene alkylaryl ether. They are uniformly dissolved to give an emulsifiable concentrate.

FORMULATION EXAMPLE 2

Wettable powder

Twenty parts of compound No. 48 of the invention, 10 parts of white carbon, 3 parts of polyoxyalkylene alkylaryl ether sulfate, 2 parts of alkylbenzenesulfonic acid salt and 65 parts of diatomaceous earth are mixed and pulverized to give a wettable powder.

FORMULATION EXAMPLE 3

Pulverulent composition

Ten parts of compound No. 67 of the invention, 10 parts of white carbon and 80 parts of fine powdery clay were mixed and pulverized to give a pulverulent composition.

FORMULATION EXAMPLE 4

Granules

Five parts of compound No. 76 of the invention, 0.5 part of sodium laurylsulfate, 3 parts of sodium ligninsulfonate, 20 parts of bentonite and 71.5 parts of talc are uniformly mixed and kneaded with a moderate amount of water. The kneaded mixture is granulated by a granulator and dried by a fluidized drying apparatus to form granules.

The following Test Examples are given to demonstrate the excellent insecticidal and acaricidal efficacy of the active compounds of formula (I) provided by this invention.

TEST EXAMPLE 1

Ovicidal test on Tetranychus urticae

Kidney bean leaf pieces were placed on a wet filter paper, and female adults of the mite were inoculated at a rate of 10 mites per leaf, and allowed to lay eggs for 24 hours. Thereafter, the female adults were removed. A chemical with a predetermined concentration (wettable powder prepared in accordance with Formulation Example 2 and diluted with water) was sprayed onto the leaf pieces and the leaf pieces were left to stand in an incubator (25° C.). Seven days later, the number of larvae hatched from the eggs was calculated under a microscope, and the ovicidal ratio was counted from the following formula. The test was conducted through 3 replicates for each area, and the results are shown in Table 2.

$$\text{Ovicidal ratio (\%)} = \frac{\left(\begin{array}{c}\text{number of}\\ \text{eggs laid}\end{array}\right) - \left(\begin{array}{c}\text{number of}\\ \text{larvae hatched}\end{array}\right)}{\text{number of eggs laid}} \times 100$$

TEST EXAMPLE 2

Ovicidal test on Tetranychus kanzawai

Kidney bean leaf pieces were placed on a wet filter paper, and female adults of the mite were inoculated at a rate of 10 mites per leaf, and allowed to lay eggs for 24 hours. Thereafter, the female adults were removed. A chemical with a predetermined concentration (emulsifiable concentrate prepared in accordance with Formulation Example 1 and diluted with water) was sprayed onto the leaf pieces and the leaf pieces were left to stand in an incubator (25° C.) Seven days later, the number of larvae hatched from the eggs was counted under a microscope, and the ovicidal ratio was calculated as in Test Example 1. The test was conducted through 3 replicates for each area, and the results are shown in Table 2.

TABLE 2

| Compound No. | Ovicidal ratio (%) | |
|---|---|---|
| | Tetranychus urticae 100 ppm | Tetranychus kanzawai 100 ppm |
| 1 | 100 | 100 |
| 2 | 100 | 100 |
| 3 | 100 | 100 |
| 4 | 90 | 90 |
| 10 | 100 | 100 |
| 11 | 100 | 100 |
| 12 | 100 | 100 |
| 13 | 100 | 100 |
| 15 | 100 | 100 |
| 16 | 100 | 100 |
| 17 | 100 | 100 |
| 18 | 100 | 100 |
| 19 | 100 | 100 |
| 21 | 100 | 100 |
| 22 | 100 | 100 |
| 23 | 100 | 100 |
| 24 | 100 | 100 |
| 26 | 100 | 100 |
| 27 | 100 | 100 |
| 28 | 100 | 100 |
| 29 | 100 | 100 |
| 30 | 100 | 100 |
| 31 | 100 | 100 |
| 33 | 100 | 100 |
| 34 | 100 | 100 |
| 36 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 67 | 100 | 100 |
| 68 | 100 | 100 |
| 69 | 100 | 100 |
| 70 | 100 | 100 |
| 71 | 100 | 100 |
| 72 | 100 | 100 |
| 73 | 100 | 100 |
| 74 | 100 | 100 |
| 75 | 100 | 100 |
| 76 | 100 | 100 |
| 77 | 100 | 100 |
| 78 | 100 | 100 |
| 79 | 100 | 100 |
| 80 | 100 | 100 |
| 81 | 100 | 100 |
| 84 | 100 | 100 |
| 85 | 100 | 100 |
| 86 | 100 | 100 |
| 87 | 100 | 100 |
| 88 | 100 | 100 |
| 89 | 100 | 100 |
| 90 | 100 | 100 |
| 91 | 100 | 100 |
| 92 | 100 | 100 |
| 93 | 100 | 100 |
| 94 | 100 | 100 |
| 95 | 100 | 100 |
| 96 | 100 | 100 |
| 97 | 100 | 100 |
| 98 | 100 | 100 |
| 99 | 100 | 100 |
| 100 | 100 | 100 |
| 101 | 100 | 100 |
| 110 | 100 | 100 |
| 117 | 100 | 100 |
| 120 | 100 | 100 |
| 121 | 100 | 100 |
| 128 | 100 | 100 |
| 129 | 100 | 100 |
| 130 | 100 | 100 |
| 131 | 100 | 100 |

TEST EXAMPLE 3

Acaricidal test on hatched larvae of Tetranychus urticae

Kidney bean leaf pieces were placed on a wet filter paper, and female adults of the mites were inoculated at a rate of 10 mites per leaf, and allowed to lay eggs for 24 hours. Thereafter, the female adults were removed. The leaf pieces were left to stand in an incubator (25° C.) Seven days later, the number of larvae hatched from the eggs was counted, and a chemical with a predetermined concentration (emulsifiable concentrate prepared in accordance with Formulation Example 1 and diluted with water) was sprayed onto the leaf pieces, and the leaf pieces were allowed to stand in an incubator (25° C.) Seven days later, the number of adults was counted under a microscope, and the acaricidal ratio on the hatched larvae was calculated from the following formula.

$$\text{Acaridical ratio (\%)} = \frac{\left(\begin{array}{c}\text{number of}\\\text{hatched}\\\text{larvae}\end{array}\right) - \left(\begin{array}{c}\text{number of}\\\text{adults}\end{array}\right)}{\text{number of hatched larvae}} \times 100$$

The test was conducted through 3 replicates for each area, and the results are shown in Table 3.

TABLE 3

| Compound No. | Insecticidal ratio (%) 100 ppm |
|---|---|
| 1 | 100 |
| 2 | 100 |
| 3 | 100 |
| 4 | 100 |
| 6 | 100 |
| 10 | 100 |
| 11 | 100 |
| 12 | 100 |
| 13 | 100 |
| 15 | 100 |
| 16 | 100 |
| 17 | 80 |
| 18 | 100 |
| 19 | 100 |
| 21 | 100 |
| 22 | 100 |
| 23 | 100 |
| 24 | 100 |
| 26 | 100 |
| 27 | 100 |
| 28 | 100 |
| 29 | 100 |
| 30 | 100 |
| 31 | 100 |
| 33 | 100 |
| 34 | 100 |
| 36 | 100 |
| 38 | 80 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |

TABLE 3-continued

| Compound No. | Insecticidal ratio (%) 100 ppm |
|---|---|
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |
| 80 | 100 |
| 81 | 100 |
| 82 | 100 |
| 83 | 100 |
| 84 | 100 |
| 85 | 100 |
| 86 | 100 |
| 87 | 100 |
| 88 | 100 |
| 89 | 100 |
| 90 | 100 |
| 91 | 100 |
| 92 | 100 |
| 93 | 100 |
| 94 | 100 |
| 95 | 100 |
| 96 | 100 |
| 97 | 100 |
| 98 | 100 |
| 99 | 100 |
| 100 | 100 |
| 101 | 100 |
| 106 | 100 |
| 110 | 100 |
| 117 | 100 |
| 121 | 100 |
| 128 | 100 |
| 129 | 100 |
| 130 | 100 |
| 131 | 80 |

TEST EXAMPLE 4

Insecticidal test on nymphs of Myzus persicae

Japanese radish seedlings in the two-main leaf stage were grown in a cup, and apterous adults of *Myzus persicae* were inoculated on the radish seedlings at a rate of 5 insects per seedling and caused to larviposit nymphs for 3 days. Then, the adults were removed, and a chemical with a predetermined concentration (a solution of the wettable powder of Formulation Example 2 diluted with water to a concentration of 500 ppm) was sprayed onto the seedlings. The treated seedlings were placed in a greenhouse, 96 hours later, the number of dead insects was counted. The insecticidal ratio was calculated in accordance with the following formula. The test was conducted through three replicates for each area, and the results are shown in Table 4.

$$\text{Insecticidal ratio (\%)} = \frac{\left(\begin{array}{c}\text{Number of}\\\text{insects parasitic}\\\text{on the plant}\\\text{before spraying}\end{array}\right) - \left(\begin{array}{c}\text{Number of}\\\text{insects parasitic}\\\text{at the time of}\\\text{examination}\end{array}\right)}{\left(\begin{array}{c}\text{Number of insects parasitic}\\\text{on the plant before spraying}\end{array}\right)} \times 100$$

TEST EXAMPLE 5

Insecticidal test on nymphs of Aphis gossypii

On cucumber seedlings in the one main leaf stage planted in a cup, apterous adults of *Aphis gossypii* were inoculated at a rate of 5 insects per seedling and caused to larviposit nymphs for 3 days. Then, the adults were removed, and a chemical with a predetermined concentration (a solution of the wettable powder of Formulation Example 2 diluted with water to a concentration of 500 ppm) was sprayed onto the seedlings. The treated seedlings were placed in a greenhouse, and the number of dead insects was counted 96 hours later. The insecticidal ratio was calculated as in Test Example 4. The test was conducted through 3 replicates for each area, and the results are shown in Table 4.

TABLE 4

| Compound No. | Insecticidal ratio (%) | |
|---|---|---|
| | Myzus persicae | Aphis gossypii |
| 1 | 100 | 100 |
| 2 | 100 | 100 |
| 3 | 100 | 100 |
| 4 | 100 | 100 |
| 10 | 100 | 100 |
| 11 | 100 | 100 |
| 12 | 100 | 100 |
| 13 | 100 | 100 |
| 15 | 100 | 100 |
| 16 | 100 | 100 |
| 17 | 100 | 100 |
| 18 | 100 | 100 |
| 19 | 100 | 100 |
| 21 | 100 | 100 |
| 23 | 100 | 100 |
| 26 | 100 | 100 |
| 27 | 100 | 100 |
| 28 | 100 | 100 |
| 29 | 100 | 100 |
| 30 | 100 | 100 |
| 31 | 100 | 100 |
| 33 | 100 | 100 |
| 34 | 100 | 100 |
| 36 | 100 | 100 |
| 38 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 67 | 100 | 100 |
| 68 | 100 | 100 |
| 69 | 100 | 100 |
| 70 | 100 | 100 |
| 71 | 100 | 100 |
| 72 | 100 | 100 |
| 73 | 100 | 100 |
| 74 | 100 | 100 |
| 75 | 100 | 100 |
| 76 | 100 | 100 |
| 77 | 100 | 100 |
| 78 | 100 | 100 |
| 79 | 100 | 100 |
| 80 | 100 | 100 |
| 81 | 100 | 100 |
| 82 | 100 | 100 |
| 83 | 100 | 100 |
| 84 | 100 | 100 |
| 85 | 100 | 100 |
| 86 | 100 | 100 |
| 87 | 100 | 100 |
| 88 | 100 | 100 |
| 89 | 100 | 100 |
| 90 | 100 | 100 |
| 91 | 100 | 100 |
| 92 | 100 | 100 |
| 93 | 100 | 100 |
| 94 | 100 | 100 |
| 95 | 100 | 100 |
| 96 | 100 | 100 |
| 97 | 100 | 100 |
| 98 | 100 | 100 |
| 99 | 100 | 100 |
| 100 | 100 | 100 |
| 101 | 100 | 100 |
| 103 | 100 | 100 |
| 109 | 100 | 100 |
| 117 | 100 | 100 |
| 130 | 100 | 100 |
| 131 | 100 | 100 |

TEST EXAMPLE 6

Insecticidal test on nymphs of Nephotettix cincticeps

A chemical (a solution prepared by diluting the wettable powder of Formulation Example 2 with water to 100 ppm) was sprayed onto rice seedlings planted in cups. After air drying, a cylindrical cover made of acrylic resin was put over each cup, and nymphs of *Nephotettix cincticeps* were released into the cup at a rate of 10 insects per seedling. The cup was closed by gauze. The treated seedlings were placed in a greenhouse. Seven days later, the number of dead insects was examined, and the insecticidal ratio was calculated as in Example 4. The test was conducted through 3 replicates for each area, and the results are shown in Table 5.

TEST EXAMPLE 7

Insecticidal test on nymphs of Nilaparvata lugens

A chemical (a solution prepared by diluting the emulsifiable concentrate of Formulation Example 1 with water to 100 ppm) was sprayed onto rice seedlings planted in cups. After air drying, a cylindrical cover made of acrylic resin was put over each cup, and nymphs of *Nilaparvata lugens* were released into the cup at a rate of 10 insects per seedling. The cup was closed by gauze. The treated seedlings were placed in a greenhouse. Seven days later, the number of dead insects was examined, and the insecticidal ratio was calculated as in Example 4. The test was conducted through 3 replicates for each area, and the results are shown in Table 5.

TABLE 5

| Compound No. | Insecticidal ratio (%) Nephotettix cincticeps | Insecticidal ratio (%) Nilaparvata lugens |
|---|---|---|
| 1 | 90 | — |
| 10 | 100 | — |
| 12 | 100 | 100 |
| 13 | 90 | — |
| 15 | 100 | 100 |
| 16 | 100 | — |
| 17 | 100 | — |
| 18 | 100 | 100 |
| 21 | 100 | — |
| 23 | 100 | — |
| 27 | 100 | — |
| 28 | 100 | — |
| 29 | 100 | 100 |
| 30 | 100 | — |
| 31 | 100 | 100 |
| 33 | 100 | 100 |
| 34 | 100 | — |
| 36 | 100 | — |
| 38 | 100 | 100 |
| 40 | 100 | 100 |
| 41 | 100 | — |
| 42 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | — |
| 61 | 100 | — |
| 62 | 100 | — |
| 63 | 100 | — |
| 65 | 100 | 100 |
| 67 | 100 | 100 |
| 68 | 100 | 100 |
| 69 | 100 | 100 |
| 70 | 100 | 100 |
| 71 | 100 | — |
| 73 | 100 | — |
| 74 | 100 | 100 |
| 75 | 100 | 100 |
| 76 | 100 | 100 |
| 79 | 90 | — |
| 80 | 100 | — |
| 81 | 100 | 100 |
| 82 | 100 | — |
| 83 | 100 | 100 |
| 84 | 100 | — |
| 85 | 100 | — |
| 86 | 100 | 100 |
| 88 | 100 | 100 |
| 89 | 100 | 100 |
| 91 | 100 | — |
| 92 | 100 | 100 |
| 93 | 100 | — |
| 95 | 100 | 100 |
| 96 | 100 | 100 |
| 97 | 100 | — |
| 98 | 100 | 100 |
| 99 | 100 | — |
| 100 | 100 | — |
| 101 | 100 | 100 |
| 117 | 100 | — |

We claim:

1. A compound represented by the following formula

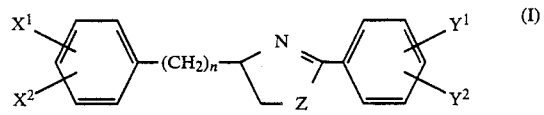

wherein
$X^1$ and $X^2$ are identical or different and each represents a hydrogen atom, a lower alkyl group, a lower alkoxy group, a fluorine atom, a chlorine atom, a bromine atom, a trifluoromethyl group or a trifluoromethoxy group;

$Y^1$ and $Y^2$ are identical or different and each represents a hydrogen atom, a lower alkyl group, a lower alkoxy group, a lower alkylthio group, a cyano group, a nitro group, a fluorine atom, a chlorine atom, a bromine atom, an iodine atom or a trifluoromethyl group;

Z represents an oxygen or sulfur atom; and, n is 0 or 1;

with the provisos that (1) $Y^1$ and $Y^2$ are not hydrogen atoms simultaneously;

(2) $Y^1$ and $Y^2$ are identical or different and each represents a lower alkyl group, a lower alkoxy group, a lower alkylthio group, a cyano group, an iodine atom or a trifluoromethyl group, when n is 0 and $X^1$ and $X^2$ are both a hydrogen atom, or when n is 1 and $X^1$ and $X^2$ are identical or different and each represents a hydrogen atom, a fluorine atom, a chlorine atom or a bromine atom; and (3) $X^1$ or $X^2$ and $Y^1$ or $Y^2$ cannot represent an alkyl group having 4 to 6 carbon atoms at the 2- or 6-position of the benzene ring.

2. The compound of claim 1 in which n is 0.

3. The compound of claim 2 in which one of $X^1$ and $X^2$ represents a hydrogen atom, and the other represents a lower alkyl group, a lower alkoxy group, a fluorine atom, a chlorine atom, a bromine atom, a trifluoromethyl group, or a trifluoromethoxy group.

4. The compound of claim 2 in which $X^1$ and $X^2$ are identical or different and each represents a lower alkyl group, a lower alkoxy group, a fluorine atom, a chlorine atom, or a trifluoromethyl group.

5. The compound of claim 1 in which $Y^1$ and $Y^2$ are identical or different and each represents a lower alkyl group, a lower alkoxy group, a fluorine atom, a chlorine atom, a bromine atom or a trifluoromethyl group.

6. The compound of claim 1 in which Z represents an oxygen atom.

7. A compound represented by the following formula

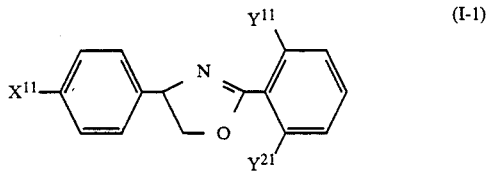

or

-continued

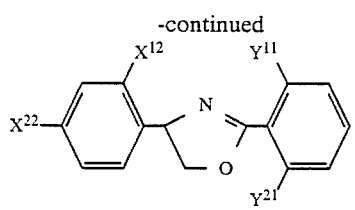
(I-2)

wherein $X^{11}$ represents a linear or branched lower alkyl group, a lower alkoxy group, a halogen atom, a trifluoromethyl group, or a trifluoromethoxy group, and $X^{12}$, $X^{22}$, $Y^{11}$ and $Y^{21}$ each represent a halogen atom.

8. An insecticide and/or an acaricide comprising the compound of formula (I) according to claim 1, and a suitable carrier therefor.

9. A method of controlling noxious insects or mites, which comprises applying an effective amount of the compound of formula (I) according to claim 1 to the insects or mites or to their habitat.

* * * * *